United States Patent
Ljubimova et al.

(10) Patent No.: US 7,547,511 B2
(45) Date of Patent: Jun. 16, 2009

(54) ANTISENSE INHIBITION OF LAMININ-8 EXPRESSION TO INHIBIT HUMAN GLIOMAS

(75) Inventors: Julia Y. Ljubimova, Studio City, CA (US); Alexander V. Ljubimov, Studio City, CA (US); Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 10/570,747

(22) PCT Filed: Sep. 13, 2004

(86) PCT No.: PCT/US2004/029956

§ 371 (c)(1),
(2), (4) Date: Jan. 30, 2007

(87) PCT Pub. No.: WO2005/028617

PCT Pub. Date: Mar. 31, 2005

(65) Prior Publication Data

US 2007/0105797 A1    May 10, 2007

Related U.S. Application Data

(60) Provisional application No. 60/502,729, filed on Sep. 12, 2003.

(51) Int. Cl.
*C12Q 1/68* (2006.01)
*C12P 19/34* (2006.01)
*C12N 5/60* (2006.01)
*C07H 21/02* (2006.01)
*C07H 21/04* (2006.01)

(52) U.S. Cl. .......... 435/6; 435/91.1; 435/325; 435/375; 536/23.1; 536/24.3; 536/24.33; 536/24.5

(58) Field of Classification Search ......... 536/23.1, 536/24.3, 24.33, 24.5; 435/6, 91.1, 325, 435/375; 514/44
See application file for complete search history.

(56) References Cited

FOREIGN PATENT DOCUMENTS

WO    2005/055980 A2    6/2005

OTHER PUBLICATIONS

Khazenzon et al. Antisense inhibition of laminin-8 expression reduces invasion of human gliomas in vitro. Molecular Cancer Therapeutics, 2003 vol. 2:985-994.*

(Continued)

*Primary Examiner*—Sean McGarry
*Assistant Examiner*—Terra Cotta Gibbs
(74) *Attorney, Agent, or Firm*—Seth D. Levy; Davis Wright Tremaine LLP

(57) ABSTRACT

Using gene array technology, we observed that an increase of the α4 chain-containing Laminin-8 correlated with poor prognosis for patients with brain gliomas. We established that inhibition of Laminin-8 expression by a new generation of highly specific and stable antisense oligonucleotides (Morpholino™) against chains of Laminin-8 could slow or stop the spread of glioma. This was demonstrated in an in vitro model using human glioblastoma multiforme cell lines M059K and U-87MG co-cultured with normal human brain microvascular endothelial cells (HBMVEC). Using Western blot analysis and immunohistochemistry, we con-firmed that antisense treatment effectively blocked laminin-8 protein synthesis. Antisense oligonucleotides against both α4 and β1 chains of laminin-8 blocked significantly the invasion of co-cultures through Matrigel. The results show that Laminin-8 may not only contribute to glioma progression and recurrence as part of the neovascularization process but also by directly increasing the invasive potential of tumor cells.

3 Claims, 8 Drawing Sheets
(4 of 8 Drawing Sheet(s) Filed in Color)

OTHER PUBLICATIONS

Fujita et al. Inhibition of laminin-8 in vivo using a novel poly(malic acid)-based carrier reduces glioma angiogenesis. Angiogenesis, 2006 vol. 9:183-191.*

Lu et al. (2005). Deliverying siRNA in vivo for functional genomics and novel therapeutics. From RNA Interference Technology (Cambridge, Appasani, ed., pp. 303-317).*

Samarsky et al. (2005). RNAi in drug development: Practical considerations. From RNA Interference Technology (Cambridge, Appasani, ed., pp. 384-395).*

Nielsen, PE. Systemic delivery. The last hurdle? Gene Therapy, 2005 vol. 12:956-957.*

Agrawal et al. Antisense therapeutics: is it as simple as complementary base recognition? Molecule Medicine Today, Feb. 2000 vol. 6:72-81.*

Gewirtz et al. Facilitating oligonucleotide delivery: helping antisense delivery on its promise. Proc. Natl. Acad. Sci., 1996 vol. 93:3161-3163.*

Ljubimova et al., Gene Array Analysis Of Differentially Expressed Genes In Human Glial Tumors. International Journal of Oncology, (2001), pp. 287-295, 18.

Ljubimova et al., Overexpression Of a4 Chain-Containing Laminins In Human Glial Tumors Identified By Gene Microarray Analysis, Cancer Research (Jul. 15, 2001), pp. 5601-5610, 61(14).

Sehgal, A., Molecular Changes During The Genesis Of Human Gliomas, Seminars In Surgical Oncology, (Jan.-Feb. 1998), pp. 3-12, 14(1).

Lal et al., A Public Database For Gene Expression In Human Cancers. Cancer Research, (Nov. 1, 1999), pp. 5403-5407, 59(21).

Miner et al., The Laminin Alpha Chains: Expression, Developmental Transitions, and Chromosomal Locations Of A1-5, Identification Of Heterotrimeric Laminins 8-11, and Cloning Of A Novel a3 Isoform, Journal of Cell Biology, (May 5, 1997), pp. 685-701, 137(3).

Colognato et al., Form And Function: The Laminin Family Of Heterotrimers, Developmental Dynamics, (Jun. 2000), pp. 213-234, 218(2).

Patarroyo et al., Laminin Isoforms In Tumor Invasion, Angiogenesis And Metastasis, Seminars . Seminars In Cancer Biology, (Jun. 2002), pp. 197-207, 12(3).

Belkin et al., Integrins As Receptors For Laminins, Microscopy Research and Technique, (Nov. 1, 2000), pp. 280-301, 51(3).

Kulla et al., Tenascin Expression Patterns and Cells Of Monocyte Lineage: Relationship In Human Gliomas, Modern Pathology, (Jan. 2000), pp. 56-67, 13(1).

Sixt et al., Endothelial Cell Laminin Isoforms, Laminins 8 And 10, Play Decisive Roles In T Cell Recruitment Across The Blood-Brain Barrier In Experimental Autoimmune Encephalomyelitis Journal of Cell Biology, (May 28, 2001), pp. 933-946, 153(5).

Thyboll et al., Deletion Of The Laminin a4 Chain Leads To Impaired Microvessel Maturation, Molecular and Cellular Biology, (Feb. 2002), pp. 1194-1202, 22(4).

Fujiwara et al., Purification And Characterization Of Human Laminin-8. Laminin-8 Stimulates Cell Adhesion And Migration Through a3β1 and a6p, Integrins, Journal of Biological Chemistry, (May 18, 2001), pp. 17550-17558, 276(20).

Gonzalez et al., Complex Interactions Between The Laminin a4 Subunit And Integrins Regulate Endothelial Cell Behavior In Vitro And Angiogenesis In Vivo, Proceedings of the National Academy of Sciences USA, (Dec. 10, 2002), pp. 16075-16080, 99(25).

Astriab-Fisher et al., Antisense Inhibition Of P- Glycoprotein Expression Using Peptide-Oligonucleotide Conjugates, Biochemical Pharmacology (Jul. 1, 2000), pp. 83-90, 60(1).

McKean et al., FAK induces Expression Of Prx1 To Promote Tenascin-C-Dependent Fibroblast Migration, Journal Of Cell Biology, (Apr. 28, 2003), pp. 393-402, 161(2).

Petajaniemi et al., Localization Of Laminin a4-Chain In Developing And Adult Human Tissues, The Journal Of Histochemistry and Cytochemistry, (Aug. 2002), pp. 1113-1130, 50(8).

Ljubimov et al., Human Corneal Basement Membrane Heterogeneity: Topographical Differences In The Expression Of Type IV Collagen And Laminin Isoforms, Lab Investigation, (Apr. 1995), pp. 461-473, 72(4).

Albini et al., A Rapid In Vitro Assay For Quantitating The Invasive Potential Of Tumor Cells, Cancer Research, (Jun. 15, 1987), pp. 3239-3245, 47(12).

Kleinman et al., Basement Membrane Complexes With Biological Activity, Biochemistry, (Jan. 28, 1986), pp. 312-318, 25(2).

Minakawa et al., In Vitro Interaction Of Astrocytes And Pericytes With Capillary-Like Structures Of Brain Microvessel Endothelium, Lab Investigation, (Jul. 1991), pp. 32-40, 65(1).

Voyta et al., Identification And Isolation Of Endothelial Cells Based On Their Increased Uptake Of Acetylated-Low Density Lipoprotein, Journal of Cell Biology, (Dec. 1984), pp. 2034-2040, 99(6).

Herold-Mende et al., Clinical Impact And Functional Aspects Of Tenascin-C Expression During Glioma Progression, International Journal Of Cancer, (Mar. 20, 2002), pp. 362-369, 98(3).

Zagzag et al., Angiogenesis In The Central Nervous System: A Role For Vascular Endothelial Growth Factor/Vascular Permeability Factor and Tenascin-C. Common Molecular Effectors In Cerebral Neoplastic And Non-Neoplastic "Angiogenic Diseases", Histol Histopathol, 17: 301-321, 2002.

Qin et al., The Transcription Factors Sp1, Sp3, and AP-2 Are Required For Constitutive Matrix Metalloproteinase-2 Gene Expression In Astroglioma Cells, Journal Of Biological Chemistry, (Oct. 8, 1999), pp. 29130-29137, 274(41).

Kachra et al., Expression Of Matrix Metalloproteinases And Their Inhibitors In Human Brain Tumors, Clinical and Experimental Metastasis, (1999), pp. 555-566, 17(7).

MacDonald et al., Urokinase Induces Receptor Mediated Brain Tumor Cell Migration And Invasion, Journal Of Neuro-Oncology, (Dec. 1998), pp. 215-226, 40(3).

Tsuj et al., Regulation Of Melanoma Cell Migration And Invasion By Laminin-5 And a3β1 Integrin (VLA-3), Clinical and Experimental Metastasis, (2002), pp. 127-134, 19(2).

Kondraganti et al., Selective Suppression Of Matrix Metalloproteinase-9 In Human Glioblastoma Cells By Antisense Gene Transfer Impairs Glioblastoma Cell Invasion, Cancer Research, (Dec. 15, 2000), pp. 6851-6855, 60(24).

Nielsen et al., Peptide Nucleic Acid Targeting Of Double-Stranded DNA. Methods In Enzymology, 2001, pp. 329-340, 340.

Dias et al., Antisense Oligonucleotides : Basic Concepts and Mechanisms, Molecular Cancer Therapy, (Mar. 2002), pp. 347-355, 1(5).

Summerton et al., Morpholino Antisense Oligomers: Design, Preparation And Properties, Antisense And Nucleic Acid Drug Development, (Jun. 1997) pp. 187-195, 7(3).

Lacerra et al., Restoration Of Hemoglobin A Synthesis In Erythroid Cells From Peripheral Blood Of Thalassemic Patients, Proceedings of the National Academy Of Sciences USA, (Aug. 15, 2000), pp. 9591-9596, 97(17).

Taylor et al., Comparison Of Efficacy Of Antisense Oligomers Directed Toward TNF-a In Helper T And Macrophage Cell Lines, Cytokine, (Sep. 1997), pp. 672-681, 9(9).

Arora et al., c- Myc Antisense Limits Rat Liver Regeneration And Indicates Role For c-myc In Regulating Cytochrome P-450 3A Activity, Journal of Pharmacology And Experimental Therapeutics, (Mar. 2000), pp. 921-928, 292(3).

Bello et al., Simultaneous Inhibition Of Glioma Angiogenesis, Cell Proliferation, And Invasion By A Naturally Occurring Fragment Of Human Metalloproteinase-2, Cancer Research, (Dec. 15, 2001), pp. 8730-8736, 61(24).

Komata et al., Combination Therapy Of Malignant Glioma Cells With 2-5A-Antisense Telomerase RNA and Recombinant Adenovirus p53, Gene Therapy, (Dec. 2000), pp. 2071-2079, 7(24).

Andrews et al., Results Of A Pilot Study Involving The Use Of An Antisense Oligodeoxynucleotide Directed Against The Insulin-Like Growth Factor Type I Receptor In Malignant Astrocytomas, Journal of Clinical Oncology, (Apr. 15, 2001), pp. 2189-2200, 19(8).

Jansen et al., Chemosensitisation Of Malignant Melanoma By BCL2 Antisense Therapy, Lancet, (Nov. 18, 2000), pp. 1728-1733, 356(9243).

Shi et al., Antisense Imaging Of Gene Expression In The Brain In Vivo, Proceeding of National Academy of Sciences USA, (Dec. 19, 2000), pp. 14709-14714, 97(26).

Boado et al., Antisense-Mediated Down-Regulation Of The Human Huntingtin Gene, Journal of Pharmacology and Experimental Therapy, (Oct. 2000), pp. 239-243, 295(1).

Knott et al., Stimulation Of Extracellular Matrix Components In The Normal Brain By Invading Glioma Cells, International Journal Of Cancer, (Mar. 16, 1998), pp. 864-872, 75(6).

De Diesbach et al., Identification, Purification and Partial Characterisation Of An Oligonucleotide Receptor In Membranes Of HepG2 Cells, Nucleic Acids Research, (Feb. 15, 2000), pp. 868-874, 28(4).

Hayashi et al., Identification And Recombinant Production Of Human Laminin a4 Subunit Splice Variants, Biochemical and Biophysical Research Communications, (Dec. 6, 2002), pp. 498-504, 299(3).

Khazenzon, A.J. et al., Novel angiogenic targets for human glioma prevention and regulation of their expression, International Journal of Molecular Medicine, 2002, 10:Supplement 1, p. S41, XP008091390.

Ljubimova, J.Y. et al., A new multifunctional drug delivery system based on polymalic acid to inhibit angiogenesis and invasion of human gliomas in vitro and in vivo, European Journal of Cancer, Supplement, 2004, 2:8, p. 184, XP004640052.

Ljubimova, J.Y. et al., Development of an vitro system to block the angiogenic target, laminin-8, in human gliomas, Proceedings of the American Association for Cancer Research Annual Meeting, Mar. 2002, vol. 43, p. 177, XP001536931.

* cited by examiner

ANTISENSE INHIBITION OF LAMININ-8 EXPRESSION TO INHIBIT HUMAN GLIOMAS

The current application is based on and claims priority from U.S. Provisional Patent Application 60/502,729, filed on Sep. 12, 2003.

This application is the National Phase of International Application PCT/US04/29956, filed Sep. 13, 2004, which designated the U.S. and that International Application was published under PCT Article 21(2) in English. This application also includes a claim of priority under 35 U.S.C. §119(e) to U.S. provisional patent application No. 60/502,729, filed Sep. 12, 2003.

INTRODUCTION

Glial tumors are the leading cause of cancer death in children [1]. Overall, they account for 1.4% of all cancers and 2.4% of all cancer deaths. Average survival time for low-grade astrocytoma or oligodendroglioma patients is 6 to 8 years. It decreases to 3 years for patients with anaplastic astrocytoma and drops to 12-18 months for glioblastoma multiforme (GBM). Currently, these tumors are treated by surgical removal, radiation therapy, chemotherapy or combinations of these treatments. The majority of GBMs is highly invasive and rapidly develops recurrences at the primary site. Tumor prognoses and responses to therapy can vary greatly even with the same histological diagnosis [2]. It is generally recognized that the improvement of prognosis, prediction of response to treatment, and development of novel effective therapeutic approaches for glial tumors may largely depend upon the introduction into clinical practice of novel specific markers involved in the development of different gliomas and their subsequent recurrences.

Attempts have been made to establish and characterize a number of glioma markers, such as glial fibrillary acidic protein, vimentin, synaptophysin, and nestin. Determination of differential expression of these markers (immunophenotyping) in gliomas, however, has thus far not altered existing therapeutic approaches, treatment success rates, or disease outcome prediction [2, 3]. Researchers next sought to identify novel glioma markers using powerful gene array technology [4-7]. Recently, our group described a new molecular marker of glial tumors, laminin-8, that was differentially expressed in malignant tumors compared to benign tumors and normal brain tissues [5].

All laminins consist of three covalently linked chains, α, β and γ. To date, 15 members (isoforms) of this family that are present in different basement membranes (BMs) have been described [8-10]. Laminins interact with cells through various receptors. Most of these receptors belong to the family of integrin heterodimers, although other molecules including dystroglycan complex and Lutheran blood group glycoprotein have also been shown to bind to laminins. In different cell types, integrins $\alpha_1\beta_1$, $\alpha_2\beta_1$, $\alpha_3\beta_1$, $\alpha_6\beta_1$, $\alpha_6\beta_4$ and $\alpha_7\beta_1$ have been reported to have the capability to bind to laminins. Specific laminin isoforms bind some but not all of these different integrins, and each integrin can bind to more than one laminin isoform [10, 11].

Along with type IV collagens, nidogens and perlecan, glycoproteins of the laminin family are the major constituents of brain microvessel BMs [8, 12, 13]. These BMs have a complex structure and are produced by both endothelial and glial cells [13]. Endothelial cells contribute laminins containing α4 and α5 chains to these BMs, whereas glial cells synthesize laminins containing α1 and α2 chains [13]. In human brain capillary BMs we have recently observed a weak expression of the α4 chain-containing laminin-9. Interestingly, during progression of human gliomas, the expression of capillary BM laminins containing α4 chain switches from the predominant laminin-9 ($\alpha 4\beta 2\gamma 1$) to laminin-8 ($\alpha 4\beta 1\gamma 1$) [5]. Laminin-8 and its receptors, integrins $\alpha_3\beta_1$ and $\alpha_6\beta_1$, appear to be important to the functioning of endothelial cell BMs, which play a role in the maintenance of the blood-brain barrier [14, 15]. Recently, the association of the laminin α4 chain with angiogenesis has been demonstrated in vivo and in vitro [16]. Some cultured glioma cell lines can also produce α4-containing laminins. Laminin-8 is thought to play a role in cell migration during development, wound healing, and angiogenesis [8, 10, 14].

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 shows Laminin α4, β1, and β2 chain expression in cells and conditioned media of pure cultures:

FIG. 3), whereas treatment with antisense oligos to either laminin α4 (antisense α4) or laminin β1 (antisense β1) chain partially inhibits both α4 and β1 chain expression (middle rows); finally, treatment with antisense oligos for both chains (antisense α4+β1) abolishes staining (lower row).

FIG. 6A, a 200-kDa band corresponding to laminin α4 chain in co-culture on days 3 and 6, and the amount of immunoreactive α4 laminin was diminished by antisense oligos to either α4 or β1 or, especially, α4+β1.

FIG. 6B, a 230-kDa band corresponding to laminin β1 chain in co-cultures on days 3 and 6, and the combination of antisense oligos (α4+β1) was efficient in decreasing the amount of immunoreactive β1 chain band at both time points.

FIGS. 6C and 6D, Western blots of fibronectin (240 kDa band) on day 6 after stripping the respective membranes from α4 and β1 chain detection and reprobing them for fibronectin (these lanes are shown for loading control purpose), and only human (but not serum) fibronectin was detected by this antibody: Lane 1, sense oligos for α4+β1 chains; Lane 2, antisense oligo for α4 chain; Lane 3, antisense oligo for β1 chain; Lane 4, antisense oligos for α4+β1 chains.

DETAILED DESCRIPTION OF THE INVENTION

Figure 1:
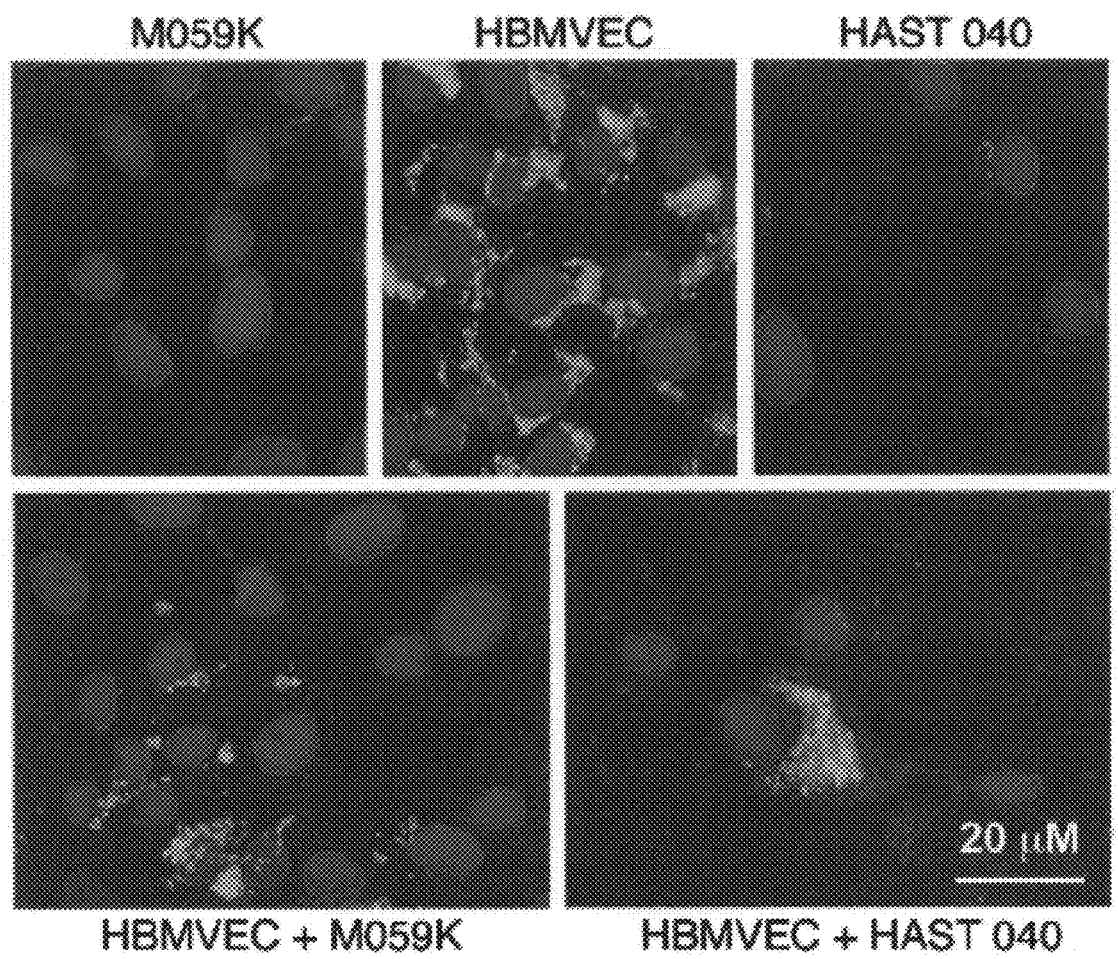
FIG. 1 shows uptake of Ac-LDL by various cultures and co-cultures; endothelial cells (HBMVEC) are positive (green fluorescence) but glioma cells (M59K) and normal astrocytes (HAST 040) are negative; in co-cultures HBMVEC+M059K and HBMVEC+HAST040, endothelial cells are positive, whereas other cells are negative (DAPI was used to counterstain cell nuclei (blue fluorescence)).

Since laminin-8 appears to be associated with GBM recurrence in vivo, we hypothesized that it might play a role in tumor invasion. Because of the complexity of in vivo experiments, we first explored this possibility in vitro using single cultures and co-cultures of brain microvascular endothelial cells, normal fetal brain astrocytes and several GBMs. We sought to analyze whether the patterns of laminin chain expression in cell culture would be similar to those seen in normal brain and in gliomas, and whether inhibition of laminin-8 expression by an antisense approach would alter glioma invasiveness through a reconstituted BM (Matrigel).

Antisense oligonucleotides (oligos) that bind and inactivate specific RNA sequences may be the best tools for studying gene function, regulation of gene expression, and interactions between gene products. Highly specific antisense oligos that mimic the DNA template for RNA production are used to bind to the complementary RNA and to prevent protein translation [17,18]. Antisense oligos are the fastest, simplest and most cost effective tools for testing new therapeutic targets for drug development. The antisense approach was used in our present study to inhibit the expression of laminin-8 in cell culture.

Our results show that normal cultured astrocytes and endothelial cells mostly express laminin-9 as seen in normal brain tissue. Glioma cells predominantly express laminin-8, again similar to the in vivo situation. Most importantly, antisense blocking of laminin-8 chain expression resulted in the inhibition of glioma invasion through Matrigel. These data show that laminin-8 is an important for glioma invasion and an effective target for antitumor therapy. That is, the differences in laminin-8 chain expression are not merely indicators of the malignant cells but are actually linked to invasiveness of the malignancy.

Co-Culture of Gliomas, Astrocytes and Brain Endothelial Cell Lines. Two types of human GBM cell lines (M059K and U-87MG; from ATCC, Rockville, Md), a normal human brain microvascular endothelial cell line (HBMVEC, obtained from Dr. Ken Samoto, Japan), and normal human fetal brain astrocytes HAST 040 (from Clonexpress, Inc., Gaithersburg, Md.) were used. U-87MG cells were cultured in Eagle's MEM with 10% fetal calf serum (FCS), L-glutamine, sodium bicarbonate, non-essential amino acids, antibiotics, and sodium pyruvate. M059K cell line was maintained in DMEM/F12 medium, FCS, supplements and antibiotics as above. The HAST 040 cell line was cultured in 50:50 DMEM/F12 supplemented with 5% FCS and antibiotics (25 µg/ml of gentamycin and 2.5 µg/ml of fungizone) during regular maintenance of astrocytes. The medium was replaced with fresh medium every third day to maintain optimal growth. HBMVEC were cultured in RPMI 1640 medium with 10% FCS, 10% NU-serum, sodium pyruvate, L-glutamine, non-essential amino acids, and antibiotics. Cell lines were maintained at 37° C. in a humidified 5% $CO_2$ incubator and subcultured with trypsin-EDTA every 3-4 days. Cell lines were co-cultured at a ratio glioma:endothelium of 5:1 in 4-well chambers and examined at different time points (24 h, 3 days, 5 days). Co-cultures of normal human astrocytes HAST 040 and HBMVEC cells were cultured at the same ratio of 5:1 in 4-well chambers and examined at different time points (24 h, 3 days, 5 days).

Antisense Treatment of Glioma-Endothelial Co-Cultures. Morpholinom™ (phosphorodiamidate morpholino oligomer) oligos custom made by Gene Tools, Inc. (St. Louis, Mo.) for laminin α☐ and β1 chains were as follows:

α4 antisense as depicted in SEQ ID NO: 1
α4 sense as depicted in SEQ ID NO: 2
β1 antisense as depicted in SEQ ID NO: 3
β1 sense as depicted in SEQ ID NO: 4

Gene Tools protocol was used according to company recommendations. The new Special Delivery Formulation consisted of a pre-paired duplex of Morpholino oligo and partially complementary DNA oligo, together with a weakly basic delivery reagent, ethoxylated polyethylenimine (EPEI). Morpholino oligos are stable and totally nuclease-resistant so there is no need for re-delivery. Co-cultures of glioma cells with normal brain endothelium were treated with anti-sense oligos to laminin-8 chains, α4 and β1, for select time intervals (3 and 6 days), alone or in combination. To make the delivery mixture, 0.5 mM antisense α4 or β1 laminin chain or 0.5 mM sense oligos (negative control) Morpholino/DNA stock solution (Gene Tools) were added to $H_2O$ and mixed. Two hundred µM EPEI Special Delivery solution was added, vortexed and incubated at room temperature for 20 min. to generate the complete delivery solution. Medium was removed from a 24-hr co-culture and the solution with a specific oligo in fresh medium was added to cells, and placed into a $CO_2$ incubator. After 3 hrs, delivery solution was aspirated and replaced with fresh serum-containing medium. Medium was changed every 2 days. Each oligo was assessed at 4 incubation time points:

2, 4, 6 and 8 days (co-culture time being 3, 5, 7, and 9 days, respectively). Another set of controls included endothelial or glioma cells alone.

Immunohistochemistry. Cells were incubated in culture with or without Morpholino and at select time periods were fixed with 4% paraformaldehyde, permeabilized with 0.2% Triton X-100, and immunostained for laminin chains and endothelial cell markers. These markers included von Willebrand factor (Sigma Chemical Co., St. Louis, Mo.), CD31 (clone HC1/6, Cymbus Biotechnology/Chemicon International, Temecula, Calif., and clone JC70A, Dako, Carpinteria, Calif.), CD34 (clone QBEnd 10, Dako), and CD105 (clone P3D1, Chemicon). Uptake of Alexa Fluor 488-labeled acetylated low-density lipoprotein (Ac-LDL, Molecular Probes, Eugene, Oreg.) was also used to identify endothelial cells. Briefly, cells were incubated for 24 hr in medium with 5 µg/ml labeled Ac-LDL, then washed, fixed and permeabilized. Cells were then counterstained with 10 ng/ml 4', 6-diamidino-2-phenylindole (DAPI, Sigma) to visualize nuclei and additionally immunostained for select laminin chains. Primary monoclonal (mAb) and polyclonal (pAb) antibodies were used to the α4 laminin chain (mAb FC10 [19], and pAb 377 [5]), β1 laminin chain (mAb LT3; Upstate Biotechnology, Lake Placid, N.Y.), and β2 laminin chain (mAb C4 obtained from the Developmental Studies Hybridoma Bank, Department of Biology, University of Iowa, Iowa City, Iowa).

Western Blot Analysis. Serum-free conditioned medium was obtained from the same number of cells in the same volume of medium from the co-cultures that were cultured for the same period of time. Conditioned media from co-cultures were concentrated 10-fold by filtering through Centriplus filtration devices (Millipore, Bedford, Mass.) and proteins were separated using 3-8% gradient Tris-acetate SDS-PAGE (Invitrogen, Carlsbad, Calif.) under reducing conditions. Lysates of human glioma T98G, known to express laminin-8 [15], were used as a positive control. The gels were blotted onto nitrocellulose membrane (Invitrogen, Carlsbad, Calif.). The membranes were probed with mAbs followed by chemiluminescent detection using the Immune-Star kit with alkaline phosphatase-conjugated secondary antibodies (Bio-Rad, Hercules, Calif.). Antibodies were used to the laminin α4 chain (mAb 8B12 [15]) and β1 chain (mAb LT3). Antibody to fibronectin $8^{th}$ type III repeat (mAb 568 [20]) was used to control for equal loading of gel lanes.

Cell Viability Assay. Cell numbers were measured with the CellTiter 96® AQueous One Solution Cell Proliferation Assay kit (Promega, Madison, Wis.). It was designed for the determination of the number of viable cells using MTS dye [3-(4,5-dimethylthiazol-2-yl)-5-(3-carboxymethoxyphenyl)-2-(4-sulfophenyl)-2H-tetrazolium, inner salt]. According to the manufacturer's instructions, a small amount of the CellTiter 96® AQueous One Solution Reagent was added directly to culture wells, and after 3 hours of incubation the absorbance at 490 nm was recorded using an ELISA reader, Spectra Max Plus 384 (Molecular Devices, Sunnyvale, Calif.). The quantity of formazan product as measured by the amount of 490 nm absorbance is directly proportional to the number of living cells in culture. All cell lines were treated exactly as described above in the section "Antisense Treatment of Glioma-Endothelial Co-Cultures". For viability assay, cells were incubated after treatment with Morpholino sense and antisense oligos and/or delivery factor for three days, the average time point that was used in our experiments. Each experiment was performed in triplicate and was repeated twice.

In Vitro Invasion Assay. Invasion studies were conducted using the Matrigel™ BM matrix assay developed for quantitative measurement of tumor cell invasiveness. Most tested cells characterized as invasive and metastatic in vivo are able to invade Matrigel in vitro [21,22,23]. We used BioCoat™ Matrigel™ invasion chambers (12-well cell culture inserts containing an 8.0 µm PET membrane with a uniform layer of Matrigel, from Becton Dickinson, Bedford, Mass.). The coated filters were rehydrated with warm serum-free DMEM (2 ml per chamber). The upper chamber was filled with 2.5× $10^4$ cells in serum-free medium. The lower chamber was filled with DMEM containing 5% FCS as a chemoattractant towards which the cells migrate. The chambers were incubated for 22 h at 37° C. in a 5% $CO_2$ atmosphere. Cells from the upper surface of the filters were removed by scrubbing with a cotton swab and those migrating to the lower surface of the filters were fixed and stained with hematoxylin and eosin. The number of cells that penetrated the filter was counted in 10 microscopic fields of each filter under ×200 magnification in both experimental and special control membranes using a Zeiss Axiophot microscope connected to an image processing and measuring system (Hamamatsu, Japan). Percent invasion is expressed as mean cell number from invasion chamber to mean cell number from control chamber according to the manufacturer's recommendation. Assays were carried out in triplicates. Four independent experiments were performed for each type of co-culture with each treatment.

Statistical analysis. The data from the cell viability assay and invasion experiments were statistically evaluated by ANOVA test using GraphPad Prism 3 software program (GraphPad Software, San Diego, Calif.). $P<0.05$ was considered significant.

Immunohistochemistry of Endothelial Markers and Laminin Chain Expression in Untreated Cultures.

Several endothelial markers were tested in order to select the best one, which might be used to reliably differentiate endothelial cells from normal and malignant astrocytes in co-cultures. In preliminary experiments, fluorescent Ac-LDL consistently labeled endothelial cells [24] much more uniformly than did antibodies against von Willebrand factor, CD31, CD34 or CD105.

Uptake of fluorescent Ac-LDL was, therefore, used to identify endothelial cells in subsequent experiments with co-cultures. In pure endothelial cultures, most if not all cells displayed predominantly punctate fluorescence with a perinuclear distribution (FIG. 1). Cultures of normal astrocytes and glioma cell lines were largely negative (FIG. 1), although some cells showed low background fluorescence. Ac-LDL uptake allowed identifying positive endothelial cells in co-cultures as well (FIG. 1).

Figure 2A:
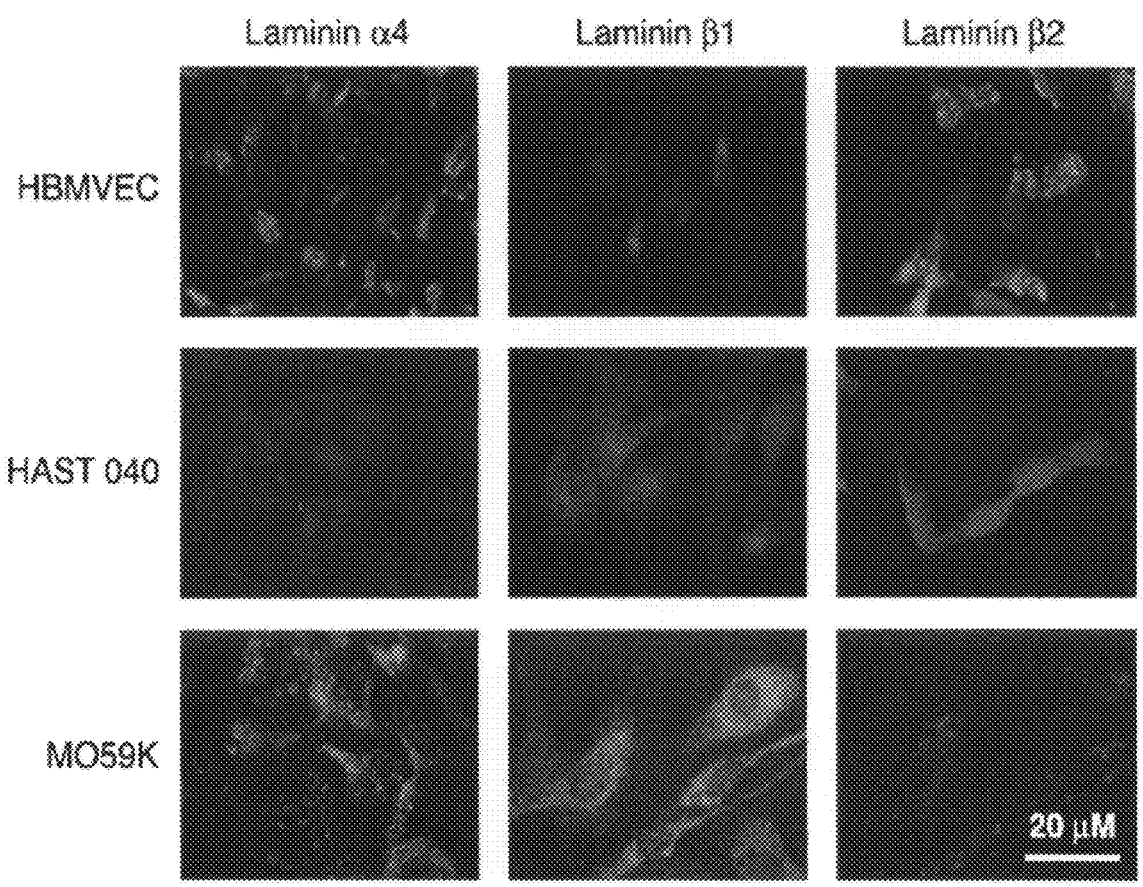
FIG. 2A. Immunolocalization of laminin chains in cells where normal brain endothelium (HBMVEC) expresses α4 and β2 chains (consistent with laminin-9, $\alpha 4\beta 2\gamma 1$), whereas astrocytes (HAST 040) do not express these laminin chains; M059K glioma cells, however, express α4 and β1 chains consistent with laminin-8 ($\alpha 4\beta 1\gamma 1$). Indirect immunofluorescence.
Figure 2B:
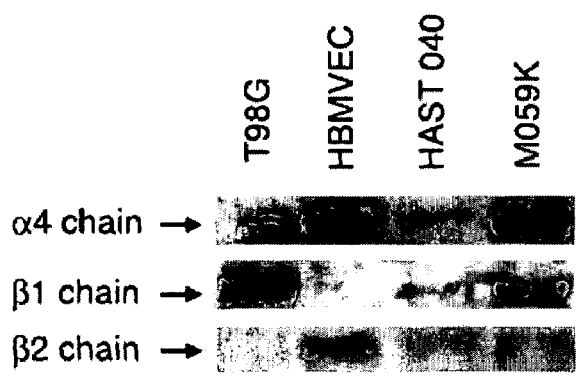
FIG. 2B. Western blot analysis of conditioned media shows that endothelial cells (HBMVEC) secrete chains of laminin-9 (α4 and β2), astrocytes (HAST 040) show little to no secretion of any studied chains, and M059K glioma cells secrete chains of laminin-8 (α4 and β1) (T98G, lysate of T98G glioma cells expressing laminin-8 chains only (α4 and β1) were used as positive control; equal amounts of conditioned media protein were applied to each lane. Note complete agreement between the results of immunostaining (FIG. 2A) and Western blotting (FIG. 2B)).

Cultures were then immunostained for chains of laminin-8 and laminin-9. In accordance with the in vivo situation, cultured normal endothelial cells stained positive for α4 and β2 chains, compatible with the presence of laminin-9 (FIG. 2A). At the same time, staining for laminin-8 β1 chain was mostly negative (FIG. 2A). Normal fetal astrocytes did not appreciably stain for any tested laminin chain (FIG. 2A). In contrast, glioma U-87MG (not shown) and M059K cells were positive for laminin-8 α4 and β1 chains but largely negative for laminin-9 β2 chain (FIG. 2A). These results were fully confirmed by Western blot analysis of conditioned media from cultures with equal protein loading (FIG. 2B).

Figure 3:
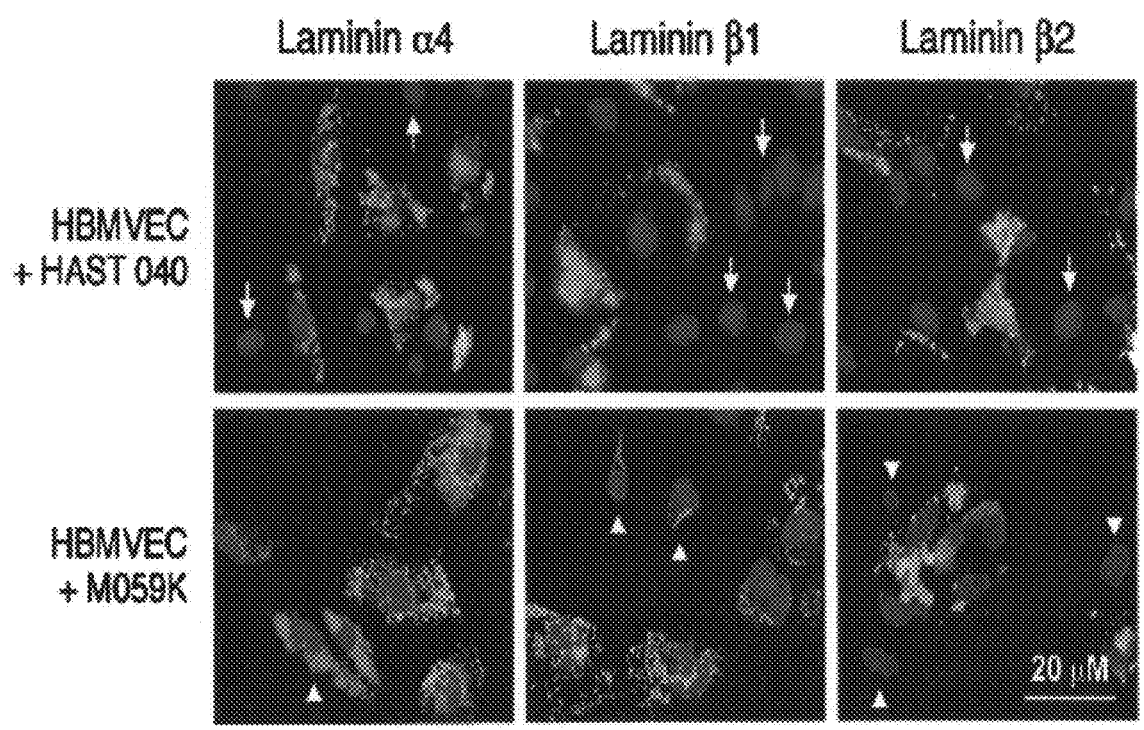
FIG. 3 shows the Laminin α4, β1, and β2 chain staining of co-cultures; live co-cultures were exposed to Ac-LDL (green color, to reveal endothelial cells) and then fixed and simultaneously stained for select laminin chains (red color) and nuclei (DAPI, blue color); in endothelial-astrocyte co-cultures (HBMVEC+HAST040) α4 and β2 chains are expressed in Ac-LDL-positive endothelial cells only but not in Ac-LDL-negative astrocytes (arrows); β1 chain is largely absent; in endothelial-glioma co-cultures (HBMVEC+M059K), α4 chain is expressed by both cell types and β2 chain, only by endothelial cells; significantly, β1 chain is expressed not only by Ac-LDL-negative glioma cells (arrowheads) but also by Ac-LDL-positive endothelial cells.

In co-cultures of normal astrocytes and HBMVEC, mostly α4 and β2 chains could be seen, with very little β1 chain expression (FIG. 3). However, in co-cultures of glioma cells with HBMVEC, α4 and β1 chains were predominantly expressed (FIG. 3). An important finding was that HBMVEC, when co-cultured with malignant astrocytes, started expressing laminin β1 chain, in contrast with its absence in endothelial cells alone or in co-culture with normal astrocytes (FIG. 3).

These data show that co-cultures of normal astrocytes and endothelial cells mostly expressed laminin-9 in accordance with our previous in vivo results [5]. Furthermore, similar to the in vivo situation, glioma cells alone and in co-cultures with endothelial cells mostly expressed laminin-8. Therefore, the established co-culture system resembled the situation in vivo in both a normal and a tumor brain environment. The laminin expression data thus strongly support the hypothesis that glioma-endothelial co-cultures is a valid model to study further the inhibition of expression of laminin-8 as a new glioma marker associated with tumor progression and recurrence development.

Figure 4:
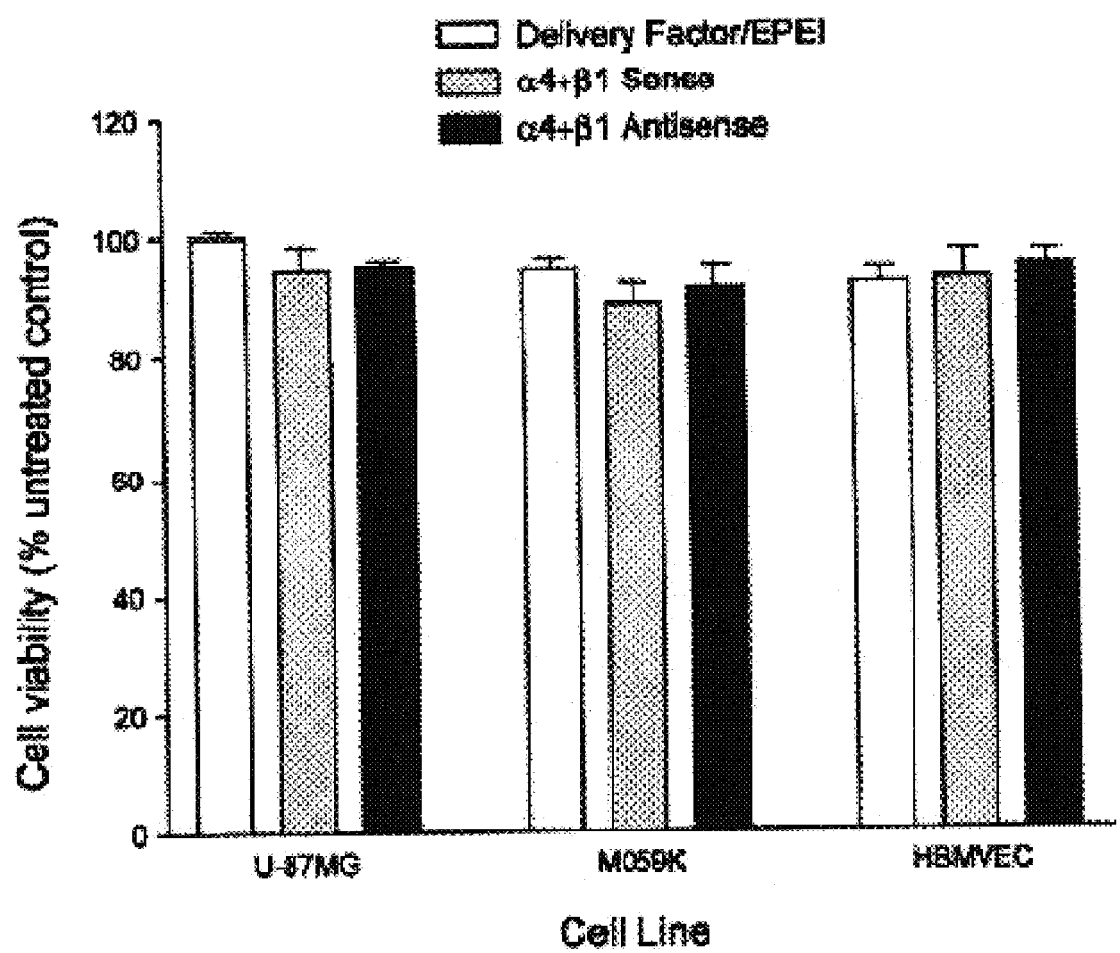
FIG. 4 shows the Cell viability assay; viability of glioma cell lines M059K and U-87MG as well as of normal endothelial cell line HBMVEC after treatment with Morpholinos sense or antisense oligos and delivery factor is higher than 90%; no significant difference from parallel untreated control cultures was detected with any treatment (cell viability without treatment was taken as 100% and cell numbers were determined using MTS assay).

Cell Viability Assay. In order to test the potential toxicity of sense and antisense Morpholino oligos and the delivery factor EPEI, cell viability was measured using MTS-based CellTiter 96 assay. The relative numbers of viable cells of three cell lines U-87MG, M059K and HBMVEC, which had been treated with oligos and/or delivery factor, were compared with cell numbers of replicate cultures of corresponding cell lines without any treatment (taken as 100%). Cell viability for each cell line after oligo treatment in two separate experiments was higher than 90% (FIG. 4). This did not differ significantly from untreated controls (p>0.05). Based on these data we conclude that Morpholinos oligos and/or delivery factor did not exert any significant toxic effect on any of the cell lines.

Figure 5:
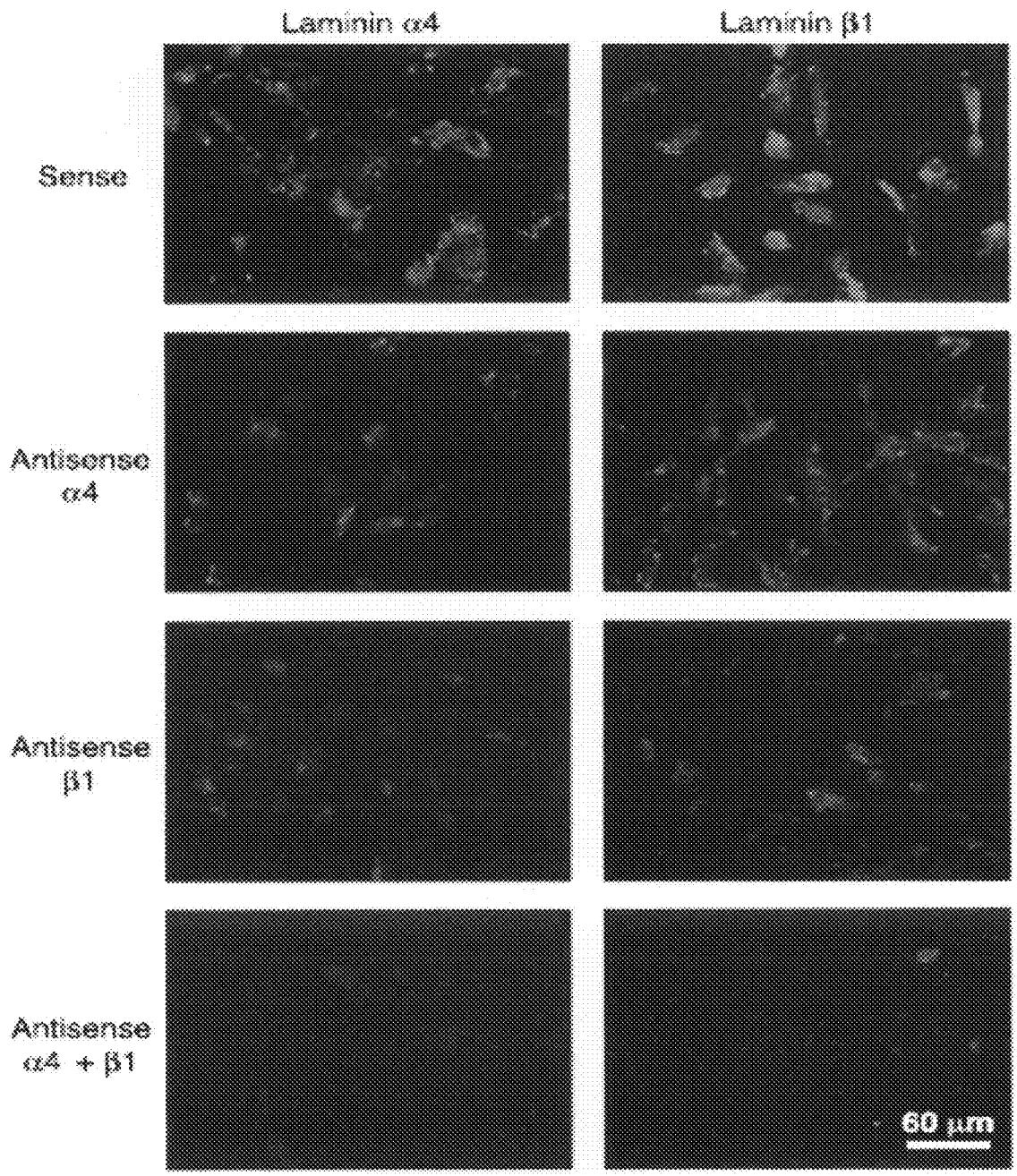
FIG. 5 shows indirect immunofluorescence Laminin α4 and β1 staining of antisense-treated co-cultures; co-cultures of M059K or U-87MG with HBMVEC treated with sense oligos to laminin α4 and β1 chains for 5 days, and the patterns of laminin chain expression are similar to untreated cultures (upper row, cf.

Immunohistochemistry of Laminin Chain Expression in Antisense-Treated Cultures. Since glioma-endothelial co-cultures mostly expressed α4 and β1 chains of laminin-8 (but not laminin-9 β2 chain), antisense oligos were used only to block laminin-8 expression. Treatment with α4 antisense resulted in markedly decreased staining for this chain and a reduction of staining for the β1 chain (FIG. 5). A similar result was seen with β1 antisense treatment, compatible with the role of this chain in laminin trimer assembly. As shown in the lower row in FIG. 5, a combination of the two oligos dramatically reduced staining for α4 and β1 chains at all time points.

Western Blot Analysis of Pure Cultures and Co-Cultures. In lysates of cultures and co-cultured cells, the signals for laminin α4 and β1 chains were very weak and detectable only on days 5-7 of culture or co-culture (data not shown). Therefore, the amounts of these chains were further analyzed in conditioned media after their substantial and equal fold concentration and normalization by total protein and fibronectin content.

Figure 6:
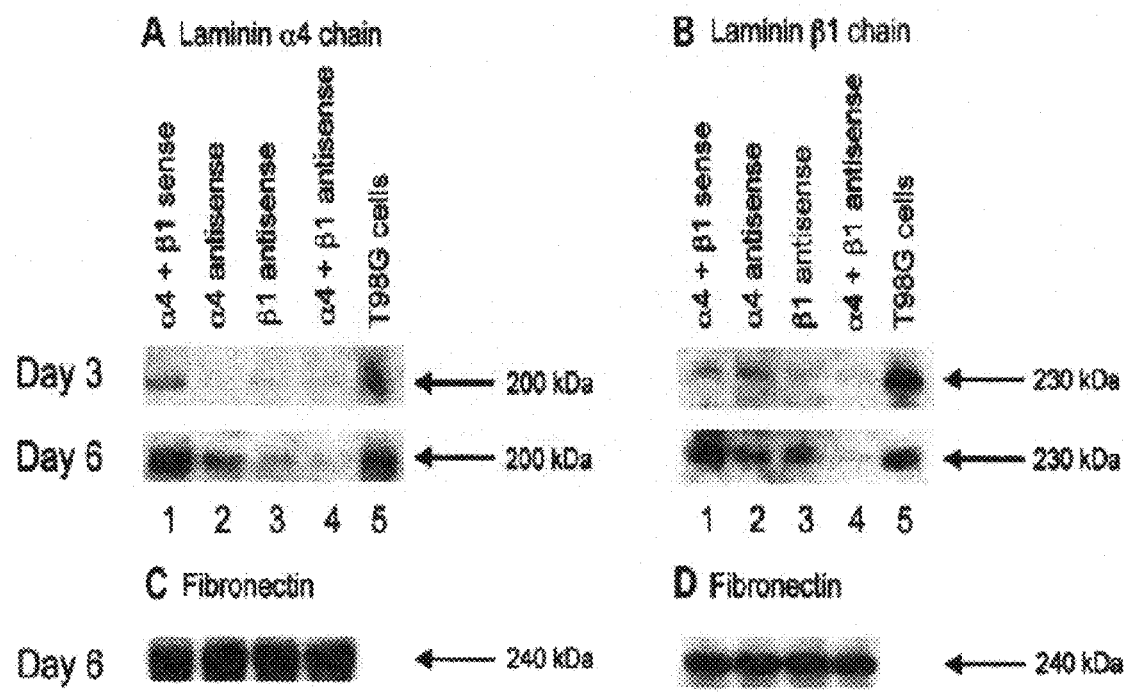
FIG. 6 shows Western blot analysis of laminin-8 α4 and β1 chains in conditioned media of co-cultured M059K and HBMVEC cells where incubation with Morpholino sense and antisense oligos was for 3 or 6 days.

As shown in FIG. 6, both α4 and β1 chains could be detected in sense-treated cultures at days 3-6, as well as in a positive control (T98G glioma cell lysate [15]). Antisense treatment of either chain resulted in a decreased signal for both chains. Again, maximum inhibition for both chains was achieved by a combined α4+β1 antisense treatment in a concentration of 0.25 mM for each oligo (FIG. 6B). These results were in complete agreement with cell immunostaining data.

FIGS. 6C and 6D show reprobing of the membranes to detect fibronectin. Only human fibronectin was detected. T98G, cell lysate of a laminin-8 expressing GBM cell line T98G, used as positive control. Very similar results were obtained using co-culture of HBMVEC with cells another glioma line, U-87MG (data not shown).

Matrigel Invasion Assay. Matrigel invasion assay was used to study the influence of antisense oligos to α4 and β1 chains of laminin-8 on the invasive parameters of co-cultures. Corresponding sense oligos were used in control chambers. Another set of controls included endothelial or glioma cells alone.

Two glioma cell lines, U-87MG and M059K, alone had, respectively, 91% and 76% of invasion potential with or without treatment with either single or combined sense oligos against α4 and β1 chains. HMBVEC cells demonstrated only 11% invasion. Each experiment was repeated three times in triplicate.

Figure 7:
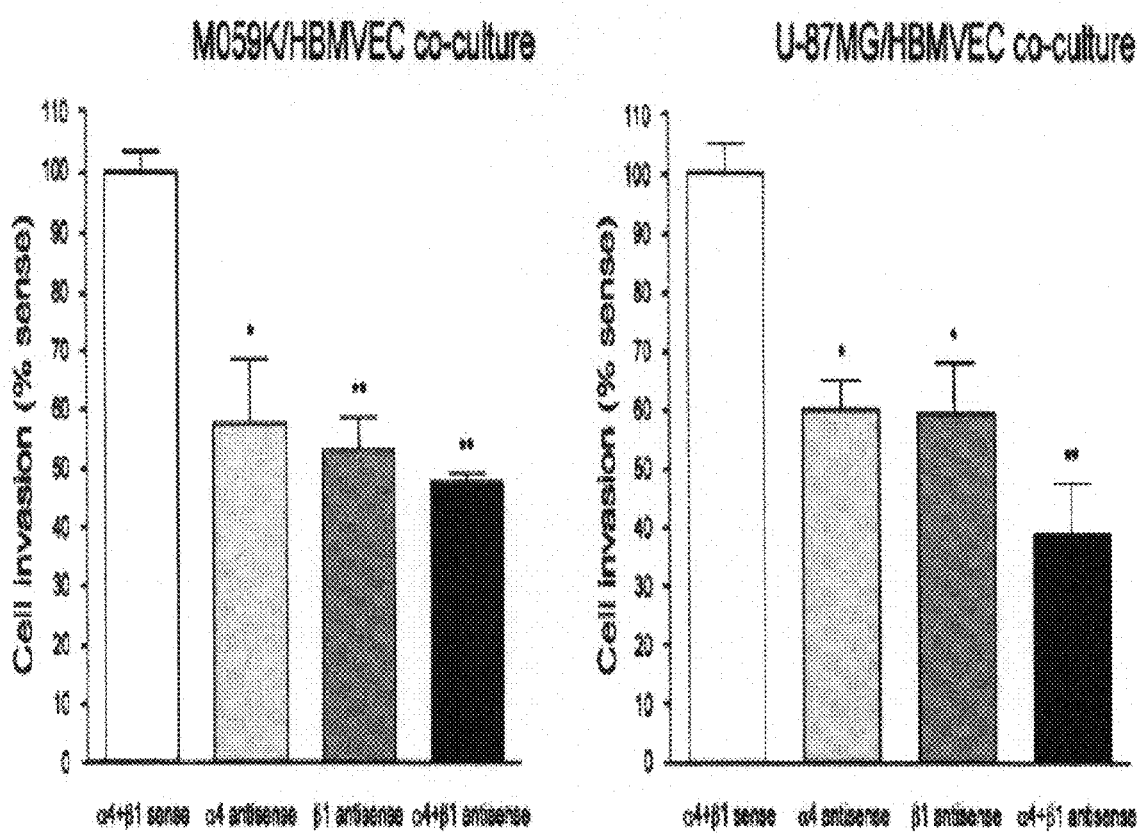
FIG. 7 shows measurement of invasion in co-cultures after antisense treatment using the Matrigel invasion assay which demonstrates a significant decrease in the fraction of cells that invaded through Matrigel in antisense-treated cultures (an even more pronounced effect is seen with a combination of antisense oligos; similar results were obtained with M059K and U-87MG glioma cell lines; *, $p<0.04$; **, $p<0.001$ by ANOVA with invasion in sense-treated cultures was taken as 100%).

In the next set of experiments, co-cultures of glioma and endothelial cells were treated for three days with α4 and β1 antisense oligonucleotides, alone or in combination. Each antisense used in this study significantly inhibited invasion of two different co-culture types (FIG. 7). In this study, 842 microscopic fields with a total of 64,276 cells were evaluated. Specific endothelial staining has demonstrated that both endothelial and glioma cells migrated through Matrigel, with clear prevalence of glioma cells (data not shown). Co-cultures treated with sense oligos to the α4 and β1 chains of laminin-8 were considered as controls equal to 100%. When co-cultures were treated with α4 antisense oligo, invasion was blocked by 40% for U-87MG (FIG. 7 right; p<0.02 vs. control) and by 41% for M059K (FIG. 7 left; p<0.03) cell lines compared to cultures treated with sense oligos (taken as 100%). β1 antisense oligo also blocked the invasion by 40% for U-87MG (p<0.04) and by about 47% for M059K (p<0.001) co-cultures. When co-cultures were treated with both antisense oligos against α4 and β1 chains, invasion was reduced on average by 62% for U-87MG (p=0.0005) and by 53% for M059K (p<0.0001) co-cultures. In two of five experiments, the inhibition exceeded 75% (not shown here).

A combination of α4+β1 antisense was more efficient at blocking laminin expression than α4 or β1 antisense in U-87MG cells and almost equal to β1 antisense in M059K cells. Interestingly, α4 and β1 chain expression was inhibited more efficiently with lower concentrations of antisense oligos (0.25+0.25 mM) than with higher ones (0.5+0.5 mM). This shows that careful optimization of Morpholino oligo concentrations is important for in vitro and in vivo studies. It is also important to emphasize the fact that only living cells can penetrate the Matrigel in the invasion assay.

Discussion

This is the first study to examine the role of laminin-8 in human tumor cell invasion using antisense inhibitors that block synthesis of this complex trimeric protein. We showed that normal brain endothelial cells expressed small amounts of laminin-9 chains, α4 and β2. The expression of laminin-8 chain, β1, however, was not detected. Normal astrocytes did not express any of these chains. This in vitro system is similar to in vivo normal brain, where there was a low expression of predominantly laminin-9 [5]. At the same time, glioma cells expressed chains of laminin-8 in culture in accordance with our previous in vivo data [5]. Moreover, in co-cultures with glioma cells, brain endothelial cells also started expressing laminin β1 chain (compatible with laminin-8 production) in agreement with the finding of laminin-8 overexpression in GBM in vivo (FIG. 3).

These data clearly show that normal and tumor in vivo patterns of α4 chain-containing laminin isoform expression were retained in the culture setting. Therefore, we were able to validate the respective co-cultures for the patterns of laminin chain expression as a system similar to that observed in vivo, both in normal brain tissue and during glioma growth. In combination with several new well-characterized proteins associated with glioma progression, such as tenascin-C, MMP-2 and MMP-9, [5, 12, 25-29], laminin-8 is an important tool for potential diagnosis or treatment of gliomas. Previously, only laminin-5 was shown to play a role in melanoma invasion [30]. Our present data show that "vascular" laminin-8 also plays a significant role in glioma cell invasiveness. Since matrix-degrading proteinases are also important for glioma invasion [31], future research should explore whether proteolysis of laminin is required for glioma invasion.

To probe the role of laminin-8 in glioma invasion, we used antisense oligos to block its expression. The potential of antisense is widely recognized, but it remained largely unfulfilled since, until recently, the available oligos suffered from poor specificity, instability, and undesirable non-antisense effects [32,33]. These problems have been largely solved by the new generation of antisense oligos that offer the promise of safe and effective therapeutics for various diseases including cancer [33,34]. The most promising types of oligos are Morpholino and peptide nucleic acid (PNA; they have nucleobases attached to a neutral "peptide-like" backbone) oligos [32,34]. Morpholino oligos function independently of RNase H and are soluble in aqueous solutions. They work well in the presence or absence of serum, are totally resistant to nucleases, and remain intact in culture medium and in cells indefinitely. Morpholino oligos have a high affinity for RNA and efficiently invade even quite stable secondary structures in mRNAs. They have the highest sequence specificity of all antisense types over a very broad concentration range and appear to be free of non-antisense effects [34,35]. They have high activity in a cell-free translation system and can block target protein production in cultured cells [36]. Morpholino are also effective in vivo [37]. Given these properties, Morpholino oligos have been chosen here to inhibit the expression of laminin-8 chains. Special experiments have demonstrated that Morpholino treatment did not affect the viability of any cell line used.

Recently, promising data on the use of antisense technology in glioma cells were obtained. The blocking of matrix metalloproteinase-9 reduced the invasiveness of glioma cells in vitro [31,38]. Glioma growth in vitro and in vivo (as xenotransplants in nude mice) could be inhibited by antisense to telomerase [39]. A recent pilot study showed that antisense to the IGF-I receptor induced glioma cell apoptosis and resulted in clinical improvement in patients [40]. Several clinical trials are currently using antisense oligos for the treatment of other cancers [41].

To examine the involvement of laminin-8 in glioma invasion, we needed reliable systems where it was possible to quantify invasion rates and to optimize the dosage of antisense laminin oligos. We used a cell culture system to meet these important needs. One could potentially use glioma cultures. To better mimic the in vivo situation, however, and because laminin-8 seems to be produced by both glioma and endothelial cells [15, FIG. 3], we needed to combine glioma cells with brain endothelium in a co-culture [44]. In such a situation, endothelial cells can develop capillary-like structures, and this process is faster when endothelial cells are cultured with tumor astrocytes than with normal embryonic brain astrocytes [45]. We hypothesized that in glioma-endothelium co-cultures there would be more laminin-8 produced, and that this laminin might increase glioma invasion in a Matrigel assay. Research into these issues should facilitate both GBM diagnosis and prognosis, and increase survival of brain cancer patients.

Matrigel invasion assay was developed for quantitative measurement of the invasiveness of tumor cells through a BM matrix. Most tested cells characterized as invasive and metastatic in vivo are able in vitro to invade Matrigel, which is a BM-like material from the mouse Engelbreth-Holm-Swarm tumor [21,22].

When glioma-endothelial co-cultures were treated by antisense, the inhibition of invasiveness on Matrigel was 62% for U-87MG+HBMVEC and 53% for M059K+HBMVEC of that seen in the control cells treated with corresponding sense oligonucleotides. In our experiments, α4 and β1 expression was inhibited more efficiently with a lower concentration of antisense oligos (0.25+0.25 mM) than with a higher concentration (0.5+0.5 mM), although no apparent toxicity was noticed at either concentration. These data may be explained by previous findings, where oligonucleotide receptors on membranes of HepG2 cells were blocked. It was shown that at relatively high oligonucleotide concentrations, these receptors were saturated and the pinocytotic process assumed larger importance [46]. A similar mechanism may occur in our system, which would explain the obtained results.

The use of antisense technology offers an effective future tumor treatment because of its efficiency, specificity and ease of delivery to tumor cells [42,43]. This technology is being continuously developed and refined not only for the drug validation and diagnostic purposes but also for the development of future treatments. The present results demonstrate the effectiveness of antisense approach using laminin-8 as a target for treatment of brain gliomas. Reduction of tumor invasion by antisense to laminin-8 slows the growth and spread of aggressive GBMs. In combination with other treatment methods or with blocking of other targets as well (EGFR, MMPs) it prolongs disease-free periods and increases survival of glioma patients. Laminin-8 blocking for therapeutic purposes may also include the use of specific monoclonal antibodies and/or small interfering RNA (siRNA) and or other drugs specific to Laminin-8 production.

It remains to be established how laminin-8 promotes glioma invasiveness. One possible mechanism may be stimulation of cell migration. It was previously shown that at least one form of laminin-8 containing α4A splice variant rather weakly supported cell adhesion and spreading compared to laminin-5 or laminin 10/11 [15, 47]. At the same time, laminin-8 stimulated cell migration better than several other laminin isoforms [15]. Increased expression of laminin-8 in both glioma cells and glioma-adjacent capillary endothelial cells [5, 15, this report] may reduce glial cell adhesion and enhance migration, which is necessary for local tumor invasiveness.

Many alterations and modifications may be made by those having ordinary skill in the art. Therefore, it must be understood that the illustrated embodiment has been set forth only for the purposes of example and that it should not be taken as limiting the invention as defined by the following claims. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, and what can be obviously substituted.

REFERENCES

1. American Cancer Society: Brain and Spinal Cord Tumors in Adults (2003).
2. Shapiro W R, Shapiro J R. Biology and treatment of malignant glioma. Oncology, 12: 233-240, 1998.
3. Kaye A H, Laws E R. (eds). Brain Tumors, pp. 990. Churchill Livingstone, 1997.
4. Ljubimova J Y, Khazenzon N M, Chen Z, Neyman Y I, Turner L, Riedinger M S, Black K L. Gene array analysis of differentially expressed genes in human glial tumors. Int J Oncol, 18: 287-295, 2001.
5. Ljubimova J Y, Lakhter A J, Loksh A, Yong W H, Riedinger M S, Miner J H, Sorokin M L, Ljubimov A V, Black K L. Overexpression of α4 chain-containing laminins in human glial tumors identified by gene microarray analysis. Cancer Res, 61: 5601-5610, 2001.
6. Sehgal A. Molecular changes during the genesis of human gliomas. Seminars Surg Oncol, 14: 3-12, 1998.
7. Lal A, Lash A E, Altschul S F, Velculescu V, Zhang L, McLendon R E, Marra M A, Prange C, Morin P J, Polyak K, Papadopoulos N, Vogelstein B, Kinzler K W, Strausberg R L, Riggins G J. A public database for gene expression in human cancers. Cancer Res, 59: 5403-5407, 1999.
8. Miner J H, Patton B L, Lentz S I, Gilbert D J, Snider W D, Jenkins N A, Copeland N G, Sanes J R. The laminin alpha chains: expression, developmental transitions, and chromosomal locations of α1-5, identification of heterotrimeric laminins 8-11, and doning of a novel α3 isoform. J Cell Biol, 137: 685-701, 1997.
9. Colognato H, Yurchenco P D. Form and function: The laminin family of heterotrimers. Dev Dyn, 218: 213-234, 2000.
10. Patarroyo M, Tryggvason K, Virtanen I. Laminin isoforms in tumor invasion, angiogenesis and metastasis. Semin Cancer Biol, 12: 197-207, 2002.
11. Belkin A M, Stepp M A. Integrins as receptors for laminins. Microsc Res Tech, 51: 280-301, 2000.
12. Kulla A, Liigant A, Piirsoo A, Rippin G. Asser T. Tenascin expression patterns and cells of monocyte lineage: relationship in human gliomas. Mod Pathol, 13: 56-67, 2000.
13. Sixt M, Engelhardt B, Pausch F, Hallmann R, Wendler O, Sorokin L M. Endothelial cell laminin isoforms, laminins 8 and 10. play decisive roles in T cell recruitment across the blood-brain barrier in experimental autoimmune encephalomyelitis. J Cell Biol, 153: 933-946, 2001.
14. Thyboll J, Kortesmaa J, Cao R, Soininen R, Wang L, livanainen A, Sorokin L, Risling M, Cao Y, Tryggvason K. Deletion of the laminin α4 chain leads to impaired microvessel maturation. Mol Cell Biol, 22:1194-1202, 2002.
15. Fujiwara H, Kikkawa Y, Sanzen N. Sekiguchi K. Purification and characterization of human laminin-8. Laminin-8 stimulates cell adhesion and migration through $α_3β_1$ and $α_6β_1$ integrins. J Biol Chem, 276: 17550-17558, 2001.
16. Gonzalez A M, Gonzales M, Herron G S, Nagavarapu U, Hopkinson S B, Tsuruta D, Jones J C. Complex interactions between the laminin α4 subunit and integrins regulate endothelial cell behavior in vitro and angiogenesis in vivo. Proc Natl Acad Sci USA, 99: 16075-16080, 2002.
17. Astriab-Fisher A, Sergueev D S, Fisher M, Shaw B R, Juliano R L. Antisense inhibition of P-glycoprotein expression using peptide-oligonucleotide conjugates. Biochem Pharmacol, 60: 83-90, 2000.
18. McKean D M, Sisbarro L, llic D, Kaplan-Alburquerque N, Nemenoff R, Weiser-Evans M, Kern M J, Jones P L. FAK induces expression of Prx1 to promote tenascin-C-dependent fibroblast migration. J Cell Biol, 161: 393-402, 2003.
19. Petäjäniemi N, Korhonen M, Kortesmaa J. Tryggvason K, Sekiguchi K, Fujiwara H, Sorokin L, Thomell L E, Wondimu Z, Assefa D, Patarroyo M, Virtanen I. Localization of laminin α4-chain in developing and adult human tissues. J Histochem Cytochem, 50: 1113-1130, 2002.
20. Ljubimov A V, Burgeson R E, Butkowski R J, Michael A F, Sun T T, Kenney M C. Human corneal basement membrane heterogeneity: Topographical differences in the expression of type IV collagen and laminin isoforms. Lab Invest, 72: 461-473, 1995.
21. Albini A, Iwamoto Y. Aaronson S A, Kozlowski J M, McEwan R N. A rapid in vitro assay for quantitating the invasive potential of tumor cells. Cancer Res, 47: 3239-3245, 1987.
22. Kleinman H K, McGarvey M L, Hassell J R, Star V L, Gannon F B, Laurie G W, Martin G R. Basement membrane complexes with biological activity. Biochemistry, 25: 312-318, 1986.
23. Minakawa T, Bready J, Berliner J, Fisher M, Cancilla P A. In vitro interaction of astrocytes and pericytes with capillary-like structures of brain microvessel endothelium. Lab Invest, 65: 32-40, 1991.
24. Voyta J, Via D, Butterfield E, Zetter B. Identification and isolation of endothelial cells based on their increased uptake of acetylated-low density lipoprotein. J Cell Biol, 99: 2034-2040, 1984.
25. Herold-Mende C, Mueller M M, Bonsanto M M, Schmitt H P, Kunze S, Steiner H H. Clinical impact and functional aspects of tenascin-C expression during glioma progression. Int J Cancer, 98: 362-369, 2002.
26. Zagzag D, Capo V. Angiogenesis in the central nervous system: a role for vascular endothelial growth factor/vascular permeability factor and tenascin-C. Common molecular effectors in cerebral neoplastic and non-neoplastic "angiogenic diseases". Histol Histopathol, 17: 301-321, 2002.
27. Qin H, Sun Y, Benveniste E N. The transcription factors Sp1, Sp3, and AP-2 are required for constitutive matrix metalloproteinase-2 gene expression in astroglioma cells. J Biol Chem, 274: 29130-29137, 1999.
28. Kachra Z, Beaulieu E, Delbecchi L, Mousseau N, Berthelet F, Moumdjian R, Del Maestro R, Beliveau R. Expression of matrix metalloproteinases and their inhibitors in human brain tumors. Clin Exp Metastasis, 17: 555-566, 1999.
29. MacDonald T J, DeClerck Y A, Laug W E. Urokinase induces receptor mediated brain tumor cell migration and invasion. J Neurooncol, 40: 215-226, 1998.
30. Tsuj T, Kawada Y, Kai-Murozono M, Komatsu S, Han S A, Takeuchi K, Mizushima H, Miyazaki K, Irimura T. Regulation of melanoma cell migration and invasion by laminin-5 and α3β1 integrin (VLA-3). Clin Exp Metastasis, 19:127-134, 2002.
31. Kondraganfi S. Mohanam S, Chintala S K, Kin Y, Jasfi S L, Nirmala C, Lakka S S, Adachi Y, Kyritsis A P, Ali-Osman F. Sawaya R, Fuller G N, Rao J S. Selective suppression of matrix metalloproteinase-9 in human glioblas- 32. Nielsen P E. Peptide nucleic acid targeting of double-stranded DNA. Methods Enzymol, 340: 329-340, 2001.
33. Dias N, Stein C A. Antisense oligonucleotides: basic concepts and mechanisms. Mol Cancer Ther, 1: 347-355, 2002.
34. Summerton J, Weller D. Morpholino antisense oligomers: Design, preparation and properties. Antisense Nucleic Acid Drug Dev, 7: 187-195, 1997.
35. Lacerra G, Sierakowska H, Carestia C, Fucharoen S, Summerton J, Weller D, Kole R. Restoration of hemoglobin A synthesis in erythroid cells from peripheral blood of thalassemic patients. Proc Natl Acad Sci USA, 97 :9591-9596, 2000.
36. Taylor M F, Paulauskis J D, Weller D D, Kobzik L. Comparison of efficacy of antisense oligomers directed toward TNF-α in helper T and macrophage cell lines. Cytokine, 9: 672-681, 1997.
37. Arora V, Knapp D C, Smith B L, Statdfield M L, Stein D A, Reddy M T, Weller D D, Iversen P L. c-Myc antisense limits rat liver regeneration and indicates role for c-myc in regulating cytochrome P-450 3A activity. J Pharmacol Exp Ther, 292: 921-928, 2000.
38. Bello L, Ludni V, Carrabba G, Giussani C, Machluf M, Pluderi M, Nikas D, Zhang J, Tomei G, Villani R M, Carroll R S, Bikfalvi A, Black P M. Simultaneous inhibition of glioma angiogenesis, cell proliferation, and invasion by a naturally occurring fragment of human metalloproteinase-2. Cancer Res, 61: 8730-6, 2001.
39. Komata T, Kondo Y, Koga S, Ko S C, Chung L W, Kondo S. Combination therapy of malignant glioma cells with 2-5A-antisense telomerase RNA and recombinant adenovirus p53. Gene Ther, 7: 2071-2079, 2000.
40. Andrews D W, Resnicoff M, Flanders A E, Kenyon L, Curtis M, Merli G, Baserga R, Iliakis G, Aiken R D. Results of a pilot study involving the use of an antisense oligodeoxynucleoide directed against the insulin-like growth factor type I receptor in malignant astrocytomas. J Clin Oncol, 19: 2189-2200, 2001.
41. Jansen B. Wacheck V, Heere-Ress E, Schlagbauer-Wadl H, Hoeller C, Lucas T, Hoermann M, Hollenstein U, Wolff K, Pehamberger H. Chemosensitisation of malignant melanoma by BCL2 antisense therapy. Lancet, 356: 1728-1733, 2000.
42. Shi N, Boado R J, Pardridge W M. Antisense imaging of gene expression in the brain in vivo. Proc Natl Acad Sci USA, 97: 14709-14714, 2000.
43. Boado R J, Kazantsev A, Apostol B L, Thompson L M, Pardridge W M. Antisense-mediated down-regulation of the human huntingtin gene. J Pharmacol Exp Ther, 295: 239-243, 2000.
44. Minakawa T, Bready J, Berliner J, Fisher M, Cancilla P A. In vitro interaction of astrocytes and pericytes with capillary-like structures of brain microvessel endothelium. Lab Invest, 65: 32-40, 1991.
45. Knott J C, Mahesparan R. Garcia-Cabrera I, Bolge Tysnes B, Edvardsen K, Ness G O, Mork S, Lund-Johansen M, Bjerkvig R. Stimulation of extracellular matrix components in the normal brain by invading glioma cells. Int J Cancer, 75: 864-872, 1998.
46. de Diesbach P, Berens C, N'Kuli F, Monsigny M, Sonveaux E, Wattiez R. Courtoy P J. Identification, purification and partial characterisation of an oligonucleotide receptor in membranes of HepG2 cells. Nucleic Acids Res, 15: 868-74, 2000.
47. Hayashi Y, Kim K H, Fujiwara H, Shimono C, Yamashita M, Sanzen N, Futaki S, Sekiguchi K. Identification and recombinant production of human laminin α4 subunit splice variants. Biochem Biophys Res Commun, 299: 498-504, 2002.

What is claimed is:

1. A method for reducing invasiveness of a human glioma in vitro comprising the step of contacting said glioma with a composition that inhibits expression of Laminin-8 by said glioma, wherein Laminin-8 expression is inhibited by inhibiting the expression of Laminin α4 chain and Laminin β1 chain of said Laminin-8, wherein the composition includes a Laminin α4 antisense polynucleotide comprising the 5' to 3' polynucleotide sequence characterized by SEQ ID NO: 1.

2. A method for reducing invasiveness of a human glioma in vitro comprising the step of contacting said glioma with a composition that inhibits expression of Laminin-8 by said glioma, wherein Laminin-8 expression is inhibited by inhibiting the expression of Laminin α4 chain and Larninin β1 chain of said Laminin-8, wherein the composition includes a Laminin β1 antisense polynucleotide comprising the 5' to 3' polynucleotide sequence characterized by SEQ ID NO: 3.

3. A method for reducing invasiveness of a human glioma in vitro comprising the step of contacting said glioma with a composition that inhibits expression of Laminin-8 by said glioma, wherein Laminin-8 expression is inhibited by inhibiting the expression of Laminin α4 chain and/or Laminin β1 chain of said Laminin-8, wherein the composition includes both a Laminin α4 antisense polynucleotide and a Laminin β1 antisense polynucleotide, wherein the Laminin β1 antisense polynucleotide includes polynucleotides comprising the 5' to 3' sequence characterized by SEQ ID NO: 3 and the Laminin α4 antisense polynucleotide includes polynucleotides comprising the 5' to 3' sequence characterized by SEQ ID NO: 1.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: alpha4 antisense

<400> SEQUENCE: 1
agctcaaagc catttctccg ctgac                                           25

<210> SEQ ID NO 2
<211> LENGTH: 25
<212> TYPE: DNA
<213> ORGANISM: Artificial sequence
<220> FEATURE:
<223> OTHER INFORMATION: alpha4 sense

<400> SEQUENCE: 2
gtcagcggag aaatggcttt gagct                                           25

<210> SEQ ID NO 3
<211> LENGTH: 25
<212> TYPE: DNA
<213> ORGANISM: Artificial Sequence

```
<220> FEATURE:
<223> OTHER INFORMATION: beta1 antisense

<400> SEQUENCE: 3
ctagcaactg gagaagcccc atgcc                                              25

<210> SEQ ID NO 4
<211> LENGTH: 25
<212> TYPE: DNA
<213> ORGANISM: Artificial Sequence
<220> FEATURE:
<223> OTHER INFORMATION: beta1 sense

<400> SEQUENCE: 4
ggcatggggc ttctccagtt gctag                                              25
```